(12) United States Patent
Belhassen et al.

(10) Patent No.: US 9,650,324 B2
(45) Date of Patent: May 16, 2017

(54) METHOD FOR THE SYNTHESIS OF KHUSIMONE

(71) Applicants: ROBERTET SA, Grasse (FR); UNIVERSITE DE NICE SOPHIA ANTIPOLIS, Nice (FR); CENTRE NATIONAL DE LA RECHERCHE SCIENTIFIQUE (CNRS), Paris (FR)

(72) Inventors: Emilie Belhassen, Saint-Laurent-du-Var (FR); Nicolas Baldovini, Nice (FR); Jean-Jacques Filippi, Nice (FR); Hugues Brevard, Grasse (FR)

(73) Assignees: ROBERTET SA, Grasse (FR); UNIVERSITE DE NICE SOPHIA ANTIPOLIS, Nice (FR); CENTRE NATIONAL DE LA RECHERCHE SCIENTIFIQUE (CNRS), Paris ( * ) Notice: Subject to any disclaimer, the term of this patent is extended or adjusted under 35 U.S.C. 154(b) by 0 days.

(21) Appl. No.: 14/902,698

(22) PCT Filed: Jun. 25, 2014

(86) PCT No.: PCT/FR2014/051605
§ 371 (c)(1),
(2) Date: Jun. 9, 2016

(87) PCT Pub. No.: WO2015/001225
PCT Pub. Date: Jan. 8, 2015

(65) Prior Publication Data
US 2016/0280622 A1    Sep. 29, 2016

(30) Foreign Application Priority Data

Jul. 3, 2013 (FR) ...................................... 13 56478

(51) Int. Cl.
*C07C 45/54* (2006.01)
*A01N 35/00* (2006.01)

(52) U.S. Cl.
CPC .......... *C07C 45/54* (2013.01); *C07C 2103/66* (2013.01); *C07C 2103/97* (2013.01)

(58) Field of Classification Search
CPC . C07C 45/54; C07C 2103/66; C07C 2103/97; A01N 35/06; A01N 45/02; A01N 65/06
USPC ......................................................... 568/342
See application file for complete search history.

(56) References Cited

FOREIGN PATENT DOCUMENTS

GB    1414704 A2 * 11/1975

OTHER PUBLICATIONS

Liu et al. Total synthesis of zizaane sesquiterpenes: (−)-khusimone, (+)-zizanoic acid, and (−)-epizizanoic acid. Canadian Journal of Chemistry, 192, vol. 60, 1081-1091.*

* cited by examiner

*Primary Examiner* — Sikarl Witherspoon
(74) *Attorney, Agent, or Firm* — Browdy and Neimark, PLLC

(57) ABSTRACT

A novel method for synthesis of khusimone, by bringing zizanal into contact with an oxidizing reagent in the presence of a base and an organic solvent.

25 Claims, 1 Drawing Sheet

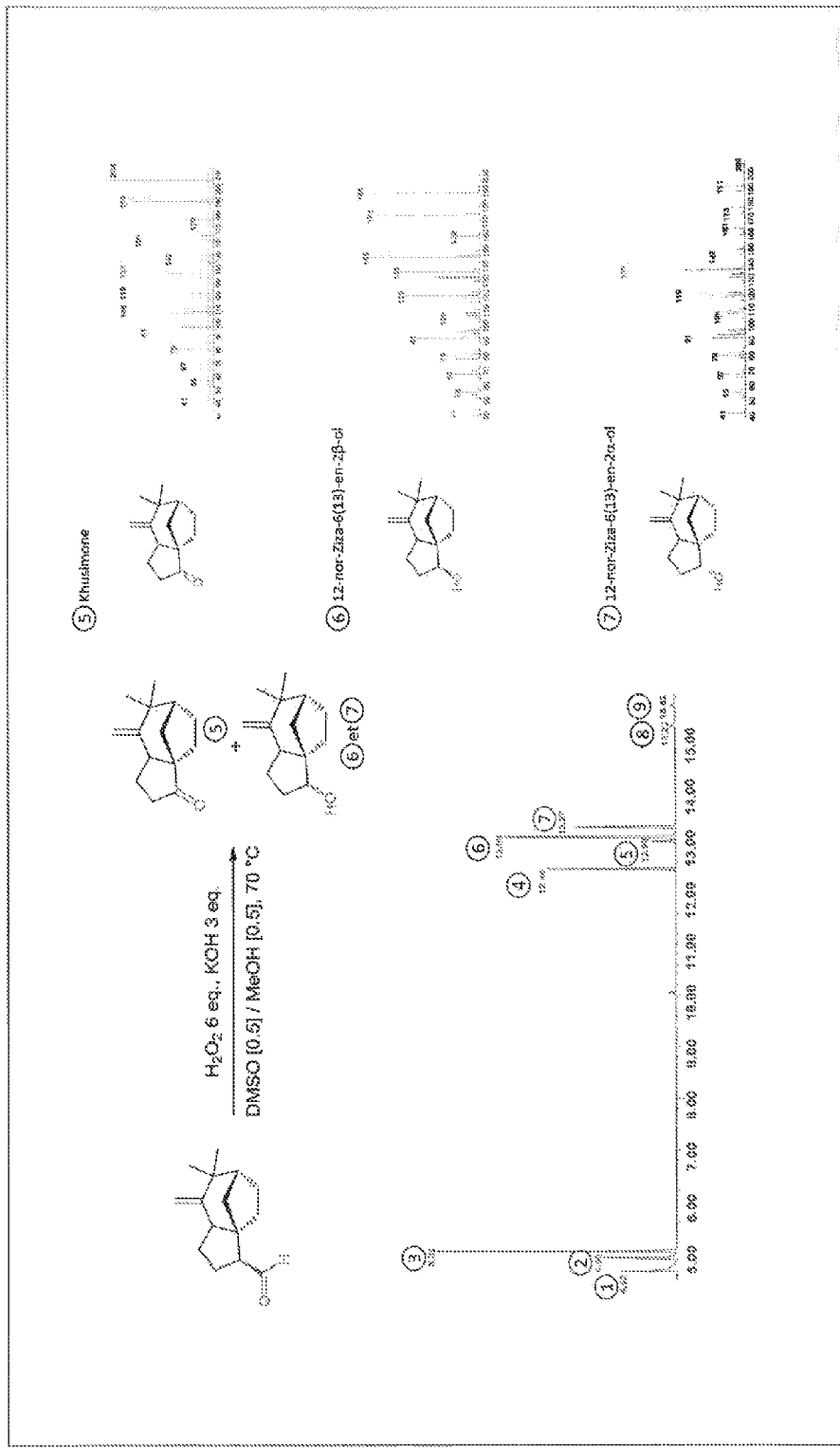

METHOD FOR THE SYNTHESIS OF KHUSIMONE

The term "Vetiver" designates in French the plants of the Poaceae (grasses) family. They consist of several species of de Chrysopogon (formerly Vetiveria) genus. A dozen species growing in tropical areas are known. The best known species is Chrysopogon zizanioides, which grows primarily in the Indian subcontinent. Two other species are frequently grown: Chrysopogon nigritanus in Southern Africa and Chrysopogon nemoralis in Southeast Asia.

The plant grows as large green tufts, and has roots, which grow vertically, that can reach depths of up to three meters (10 ft).

After distillation, the Vetiver roots produce a highly viscous essential oil used in perfumery. Vetiver essence is a fine and complex fragrance: woody, aromatic, green, earthy, sometimes slightly smoky or citrus-like.

Many fragrances on the market contain Vetiver essential oil, or derivatives thereof, as the key aromatic ingredient, such as vetiveryl acetates.

At present, no synthetic aromatic material corresponding to Vetiver essential oil is commercially available.

The lack of a synthetic substitute is partly due to the complex nature of Vetiver essence components.

Olfactometry studies conducted by the applicant on different Vetiver extracts, components, and derivatives have identified a number of main compounds that have an aromatic impact. Among these molecules affecting aroma, those having a zizaane backbone occupy a special place, including khusimone and its isomer (otherwise collectively referred to herein as Khusimone), whose structures correspond to the formula I below

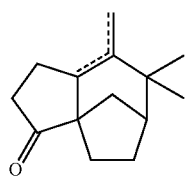

I

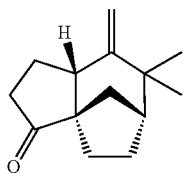

I' and particularly the isomer with Formula I' which is known as one of the main aromatic ingredients in Vetiver. This substance has a woody odor, typical of Vetiver and reminiscent of the smell of Vetiver essential oil.

For these reasons, khusimone synthesis has quickly become of great interest, not only due to the challenged presented by its synthesis as to the development of its tricyclic ring, which has several stereogenic centers, but also due to its use potential in the perfumery industry. A number of full syntheses performed at the academic level have been published, but their upscaling to the industrial level represents a special challenge.

However, khusimone semisynthesis from zizanoic acid, or from its iso-form, with Formula II below,

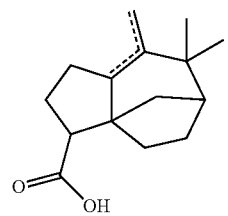

II is much more promising.

Indeed, this acid is naturally present, at levels of more than 10% in some Vetiver extracts, particularly in essential oils, and can be selectively isolated by simple acid/base wash.

Three methods are known in the prior art that lead to the zizanoic acid conversion into khusimone:

FR2 201 841 (May 3, 1974) describes the zizanoic acid transformation into khusimone by oxidative decarboxylation of zizanoic acid into 12-norziza-6(13)-en-2β-yl acetate with lead tetraacetate. This acetate can then be saponified and oxidized to khusimone. The use of 12 equivalents of lead tetraacetate in the first step makes industrialization of this synthesis pathway impossible due to its cost and its environmental incompatibility.

In 1980, Maurer B. (Seifen Ole Fette Wachse; 106. Jg 1980, 13, 347) suggested an alternative approach in which methyl zizanoate, treated with potassium tert-butoxide, reacts with oxygen to yield an α-hydroxylation product that can then be degraded to khusimone.

In 1982, Hsing-Jang Liu et al. (Can. J. Chem., vol. 60, 1982) described the preparation of zizanoic acid by bringing zizanal into contact with an oxidizing reagent, Jones reagent, whose residual chromium compounds are very toxic.

In 1989, Sakurai et al. (Sakurai et al., Agric. Biol. Chem., 1989, 53 (5), 1449-1450) published the electrochemical conversion of zixanoic acid to khusimone. The poor yields and low conversion rate of this synthesis pathway makes it unsatisfactory for industrialization.

Thus, there continues to be a need for khusimone synthesis pathways that are easily scaled to the industrial level because the reagents used are economic, ecological and consistent with public health, or else a synthesis pathway that could prevent the use of an often expensive catalyst by the operator and that usually makes scaling up of the reaction to the industrial level almost impossible.

It is one of the objectives of the present invention. In fact, the inventors have found an original method for the semi-synthesis of khusimone. The nature of the reagents and the conditions used allow considering that this new synthesis pathway can be adapted to an industrial level and is quite competitive.

The inventors have discovered that zizanal, with formula III,

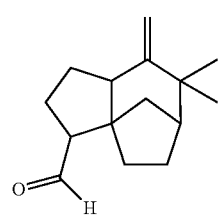

III shows unexpected reactivity, and that it is possible to form a mixture of khusimone (I) and the corresponding alcohols, 12-norziza-6(13)-en-2α-ol and 12-norziza-6(13)-en-2β-ol (or 12-norzizaenols) (IV) by oxidative decarbonylation of said zizanal (III) according to the following reaction diagram:

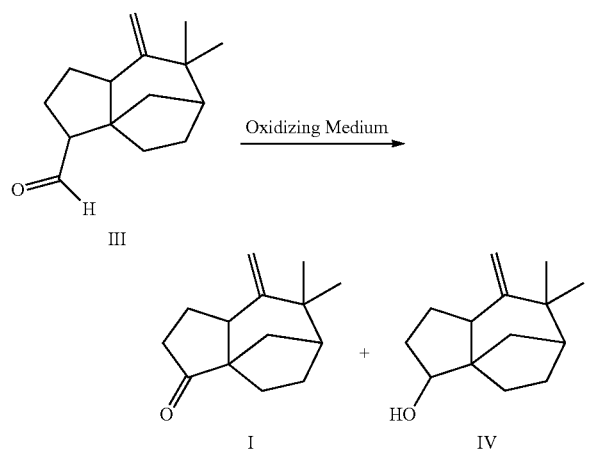

Because the reagents are very economical, non-toxic and non-polluting, this semisynthesis method seems particularly suitable for the industrial production of khusimone. Moreover, this reaction can be carried out in the absence of a catalyst. In this way, the invention relates primarily to the synthesis of khusimone by decarbonylation of zizanal with an oxidizing reagent.

In a first embodiment, the reaction can be carried out in the presence of a base.

In another embodiment, the reaction can be carried out in the presence of a solvent, preferably an organic solvent.

In yet another embodiment, preferably, the reaction can be carried out in the presence of a base and an organic solvent.

More specifically, the invention relates to the synthesis of khusimone by the oxidative decarbonylation of zizanal, which includes the reaction of zizanal in the presence of a primary oxidizing reagent, such as a peracid, or a peroxide, or a mixture, preferably in the presence of a base or of a solvent, most preferably in the presence of a base and a solvent, said solvent being preferably an organic solvent.

By a mixture it is understood a mixture of peracids, or a mixture of peroxides, or a mixture of peracids and peroxides, themselves being alone or a mixture.

According to the invention, said oxidizing reagent can be selected from hydrogen peroxide, tert-butyl hydroperoxide, di-tert-butyl peroxide, dicumyl peroxide, tert-butyl cumyl peroxide, dibenzoyl peroxide, dilauryl, di-(2,4-dichlorobenzoyl), tert-butyl hydroperoxide, cumyl, 1-phenylethyl, performic acid, peracetic acid, perpropionic acid, m-chloroperbenzoic acid, monoperphthalic acid, monopermaleic acid or trifluoroperacetic acid.

Preferably, said oxidizing reagent is hydrogen peroxide.

According to the invention, the oxidative decarbonylation reaction of zizanal can be carried out with a molar ratio [(OR)/(Z)] between the oxidizing reagent (OR) and zizanal (Z) that can be between 0.1 and 50, preferably between 0.5 and 25, more preferably between 1 and 10, preferably equal to 6.

According to the invention, the base can be selected from sodium hydroxide (NaOH), potassium hydroxide (KOH), sodium methanolate (MeNaO), sodium ethoxide (EtONa), potassium tert-butoxide (KOtBu), calcium hydroxide (Ca(OH)$_2$), ammonia, lithium hydroxide (LiOH).

Preferably, said base can be sodium hydroxide or potassium hydroxide, more preferably potassium hydroxide.

According to the invention, the oxidative decarbonylation reaction of zizanal can be carried out with a molar ratio [(B)/(Z)] between the base (B) and zizanal (Z) that can be between 0.1 and 50, preferably between 0.5 and 25, more preferably between 1 and 10, preferably equal to 3.

According to the invention, said solvent can be selected from water, methanol, ethanol, propanol, isopropanol, n-butanol, sec-butanol, isobutanol, tert-butanol, tetrahydrofuran (THF), dioxane, methyl tert-butyl ether (MTBE), diethyl ether (Et$_2$O), glyme, diglyme, dichloromethane (CH$_2$Cl$_2$), chloroform (CHCl$_3$), dimethylsulfoxide (DMSO), acetonitrile, ethyl acetate, isopropyl acetate, or mixtures of any kind (binary, ternary, etc.) and in all proportions of these solvents, for example, binary mixtures of DMSO/methanol, THF/methanol, DMSO/THF, DMSO/Dioxane. Preferably, said organic solvent can be methanol or a mixture in all proportions of MeOH/DMSO, more preferably a 1:1 mixture of MeOH/DMSO.

According to the invention, the oxidative decarbonylation reaction of zizanal can be carried out with a reaction mixture containing all sorts of zizanal concentrations. Thus, according to the invention, the oxidative decarbonylation reaction of zizanal can be carried out with a range of zizanal concentrations in the reaction mixture, from 0.01 to 4.5M, preferably between 0.02 and 0.07M, more preferably 0.2M.

It is also possible not to use any solvent at all or very little solvent. Thus, in an embodiment of the invention, the oxidative decarbonylation reaction of zizanal can be carried out without solvent.

According to the invention, the oxidative decarbonylation reaction of zizanal can be carried out at a temperature between −25° C. (13° F.) and the solvent reflux temperature. Preferably, the reaction can be started at a temperature between −25° C. and 25° C. (13° F. to 77° F.), more preferably −25° C. and 0° C. (13° F. to 32° F.). The reaction can then progress freely until it reaches solvent reflux temperature; it can then be kept at a temperature between 25° C. (77° F.) and the reflux temperature, until all reactants are exhausted. Most preferably, once the solvent reflux temperature has been reached, the reaction can be kept at this temperature.

Those skilled in the art will readily stop the reaction when it can be observed, by sample collection and analysis, that the reaction has reached the desired stage, for example, by measuring the partial or total consumption of zizanal with gas chromatography or thin layer chromatography, or by nuclear magnetic resonance. For example the reaction can be stopped by adding an aqueous solution and an organic solvent, or even just by solvent evaporation. The aqueous solution can be, for example, a calcium carbonate solution, or even a reducing aqueous solution, acid, neutral or base (such as a hydrochloric acid solution or a sodium thiosulfate solution). The solvent comprising the organic phase can be, for example, ethyl acetate, diethyl ether or petroleum ether, MTBE, cyclohexane, hexane, pentane, THF, or even dichloromethane. It is also possible to proceed to silica/Celite filtration, or just solvent evaporation.

At this stage of the invention, the mixture obtained after the oxidative decarbonylation of zizanal and addition of the stop solution can be used directly, or the mixture 12-norzizaenols (IV)/khusimone (I) can be isolated from the reaction medium obtained after the oxidative decarbonylation of zizanal.

According to the invention, the oxidative decarbonylation reaction of zizanal starts with the addition of the reagents. The reaction may be carried out for several days without product degradation.

As indicated above, the oxidative decarbonylation reaction of zizanal leads to a mixture containing the khusimone and 12-norzizaenols. The yields and the 12-norzizaenols (IV)/khusimone (I) ratio at the end of the reaction vary depending on the base type and the number of equivalents of reagents used. It is also observed that the 12-norzizaenols (IV)/khusimone (I) ratio varies depending on the solvent used. In fact, when methanol alone is used, khusimone is predominantly observed, while the use of a DMSO/MeOH mixture produces more 12-norzizaenols than khusimone.

All methods known to those skilled in the art to isolate the 12-norzizaenols (IV)/khusimone (I) mixture can be used according to the invention.

Once isolated, the 12-norzizaenols (IV)/khusimone (I) mixture may be submitted to oxidation in the presence, for example, of an oxidant (O) selected from tetrapropylammonium perruthenate or alkali hypochlorites, such as, for example, calcium or sodium hypochlorite, manganese oxide, dichromate or pyridinium chlorochromate, ceric ammonium nitrate (CAN), Collins reagent, chromium trioxide, 2,3-dichloro-5,6-dicyano-p-benzoquinone (DDQ), 2,4,6-trichloro-1,3,5-triazine, a mixture of dimethyl sulfoxide (DMSO) and oxalyl chloride (Swern Oxidation), a mixture of DMSO and pyridine sulfur trioxide (Parikh-Doering Oxidation), a mixture of DMSO and trifluoroacetic anhydride, a mixture of DMSO and acetic anhydride, a mixture of DMSO and phosphorus oxide ($P_2O_5$), a mixture of dimethyl sulfide and N-chlorosuccinimide ($Me_2S$/NCS Corey-Kim Oxidation), a mixture of $H_2O_2$ and potassium bicarbonate ($KHCO_3$) (Fleming Oxidation), Dess-Martin periodinane or acetoxyiodine oxide, 2-iodoxybenzoic acid, aluminum isopropoxide, an oxidizing system containing TEMPO (2,2,6,6-Tetramethylpiperidine-1-oxyl), or tetrapropylammonium perruthenate (TPAP) and N-methylmorpholine-N-oxide, preferably tetrapropylammonium perruthenate and, optionally, a co-oxidant, such as, N-methylmorpholine N-oxide (NMO) in the presence an organic solvent selected from dichloromethane (DCM), diethyl ether, DMSO, toluene, tetrahydrofuran (THF), or acetone, acetonitrile, water, or a mixture in all proportions of the listed solvents, preferably DCM, acetone, DMSO and water, or a mixture in all proportions of the listed solvents.

This oxidation is intended to convert 12-norzizaenols (IV) into khusimone (I).

Other characteristics and advantages of the invention will emerge from the following examples, given as illustrations, but not by way of limitation, as well as from the attached FIGURE, which represents the gas chromatography analysis results of the oxidative decarbonylation reaction of zizanal in the presence of hydrogen peroxide.

EXAMPLES

Example 1

Synthesis of Khusimone from Zizanal in the Presence of Hydrogen Peroxide ($H2O2$)

In a flask, 1 equivalent of zizanal is mixed with 6 equivalents of hydrogen peroxide (35% w/w in water) and 3 equivalents of potassium hydroxide (6N in water) until a final zizanal concentration of 0.2 mol/L was reached in the reaction mixture, which further contains a 1:1 mixture of MeOH/DMSO, at the reflux temperature (76° C. [169° F.]) for 4 hours.

The progress of the reaction can be monitored by analyzing samples of the reaction medium. Once the desired conversion is reached, a saturated of sodium bicarbonate ($NaHCO_3$) solution was added to the reaction medium. Next, an equivalent amount of diethyl ether was added. The organic phase is recovered. Hydrochloric acid (HCl), 2M, is added to the aqueous phase in order to reach an acidic pH (almost 0); next, this acidified aqueous phase is re-extracted 3 times with diethyl ether. Once combined, the organic phases are washed with brine and then dried with magnesium sulfate, and finally filtered for evaporation.

The result of this reaction is shown in the FIGURE, in which we can see the monitoring chromatogram for this reaction. The total disappearance of the starting material was observed (Zizanal), as well as the presence of 12-norzizaenol [peaks (6) and (7)] and khusimone [peak (5)], which are quantified using two internal references, anisole (peak 3) and hexadecane (peak 4). The chromatogram revealed the peak of an unknown product (1), a peak corresponding to dimethyl sulfone (peak 2) and 2 peaks [(8 and (9)] corresponding respectively to zizanal dimethyl acetal (peak 8) and zizanoic acid (peak 9).

These results were also confirmed by product purification by passage through a silica column.

The resulting mixture is composed of 6% khusimone, 75% of 12-norzizaenols, and 1% zizanal dimethyl acetal Example 2

Synthesis of Khusimone from the Khusimone/Zizaenol Mixture Obtained in Example 1

In a flask, 1 equivalent of the zizaenol/khusimone mixture obtained in Example 1 is mixed with 0.01 equivalent of tetrapropylammonium perruthenate (TPAP) and 0.7 equivalents of N-methylmorpholine N-oxide (NMO) in dichloromethane (DCM) (to have a mixture concentration of 0.35 mol/L) at room temperature for 30 minutes. The reaction medium is filtered through silica, with ether and then evaporated. In this way, khusimone is obtained with a 94% yield.

The invention claimed is:

1. Khusimone synthesis method by bringing together zizanal and an oxidizing reagent.

2. Method of claim 1, wherein zizanal is brought together with an oxidizing reagent in the presence of a base.

3. Method of claim 1, wherein zizanal is brought together with an oxidizing reagent in the presence of an organic solvent.

4. Method of claim 1, wherein zizanal is brought together with an oxidizing reagent in the presence of a base and an organic solvent.

5. Method of claim 1, wherein said oxidizing reagent is a peracid or peroxide, or a mixture.

6. Method of claim 1, wherein said oxidizing reagent can be selected from hydrogen peroxide, tert-butyl hydroperoxide, di-tert-butyl peroxide, dicumyl peroxide, tert-butyl cumyl peroxide, dibenzoyl peroxide, dilauryl, di-(2,4-dichlorobenzoyl), tert-butyl hydroperoxide, cumyl, 1-phenylethyl, performic acid, peracetic acid, perpropionic acid, m-chloroperbenzoic acid, monoperphthalic acid, monopermaleic acid or trifluoroperacetic acid.

7. Method of claim 1, wherein the molar ratio [(OR)/(Z)] between the oxidizing reagent (OR) and zizanal (Z) is between 0.1 and 50.

8. Method of claim 1, wherein the molar ratio [(OR)/(Z)] between the oxidizing reagent (OR) and zizanal (Z) is between 0.5 and 25.

9. Method of claim 1, wherein the molar ratio [(OR)/(Z)] between the oxidizing reagent (OR) and zizanal (Z) is between 1 and 10.

10. Method of claim 1, wherein the molar ratio [(OR)/(Z)] between the oxidizing reagent (OR) and zizanal (Z) is equal to 6.

11. Method of claim 2, wherein said base can be selected from sodium hydroxide (NaOH), potassium hydroxide (KOH), sodium methanolate (MeNaO), calcium hydroxide (Ca(OH)2), lithium hydroxide (LiOH).

12. Method of claim 2, wherein the molar ratio [(B)/(Z)] between the base (B) and zizanal (Z) is between 0.1 and 50.

13. Method of claim 2, wherein the molar ratio [(B)/(Z)] between the base (B) and zizanal (Z) is between 0.5 and 25.

14. Method of claim 2, wherein the molar ratio [(B)/(Z)] between the base (B) and zizanal (Z) is between 1 and 10.

15. Method of claim 2, wherein the molar ratio [(B)/(Z)] between the base (B) and zizanal (Z) is equal to 3.

16. Method of claim 3, wherein said solvent is selected from water, methanol, ethanol, 5 propanol, isopropanol, n-butanol, secbutanol, isobutanol, tert-butanol, tetrahydrofuran (THF), 1,4-dioxane, methyl tert-butyl ether (MTBE), diethyl ether ($Et_2O$), glyme, diglyme, dichloromethane ($CH_2Cl_2$), chloroform ($CHCl_3$), dimethylsulfoxide (DMSO), acetonitrile, ethyl acetate, isopropyl acetate, or mixtures in any proportions of these solvents.

17. Method of claim 1, wherein the zizanal concentration in the reaction mixture is between 0.01 and 4.5M.

18. Method of claim 1, wherein the zizanal concentration in the reaction mixture is between 0.02 and 0.07M.

19. Method of claim 1, wherein the zizanal concentration in the reaction mixture is 0.2M.

20. Method of claim 1, wherein the reaction is carried out at a temperature between −25° C. (13° F.) and the solvent reflux temperature.

21. Method of claim 1, wherein an oxidation step of an 12-norzizaenol (IV)/khusimone (I) mixture obtained after the decarbonylation reaction in an oxidizing medium is involved.

22. Method of claim 21, wherein the oxidizing step of the 12-norzizaenol (IV)/khusimone (I) mixture is carried out in the presence of an oxidizing medium (0) and an organic solvent.

23. Method of claim 22, wherein the oxidizing medium (0) is selected from tetrapropylammonium perruthenate, manganese oxide, pyridinium chlorochromate, ceric ammonium nitrate (CAN), pyridinium dichromate, Collins reagent, chromium trioxide, 2,3-dichloro-5,6-dicyano-p-benzoquinone (DDQ), 2,4,6-trichloro-1,3,5-triazine, DMSO, a mixture of DMSO and oxalyl chloride, a mixture of mixture of DMSO and pyridine sulfur trioxide, a mixture of DMSO and trifluoroacetic anhydride, a mixture of DMSO and acetic anhydride, a mixture of DMSO and phosphorus oxide ($P_2O_5$), a mixture of dimethyl sulfide and N-chlorosuccinimide ($Me_2S$/NCS Corey-Kim Oxidation), a mixture of $H_2O_2$ and potassium bicarbonate ($KHCO_3$) (Fleming Oxidation), Dess-Martin periodinane or acetoxyiodine oxide, 2-iodoxybenzoic acid, aluminum isopropoxide, an oxidizing system containing TEMPO (2,2,6,6-Tetramethyl-piperidine-1-oxyl), or tetrapropylammonium perruthenate (TPAP) and N-methylmorpholine-N-oxide and, optionally, a co-oxidant.

24. Method of claim 22, wherein the oxidizing medium (O) is N-methylmorpholine N-oxide (NMO).

25. Method of claim 22, wherein the organic solvent is selected from dichloromethane (DCM), diethyl ether, DMSO, toluene, tetrahydrofuran (THF), or acetone, acetonitrile, water, or a mixture in all proportions of the listed solvents, or a mixture in all proportions of the listed solvents.

* * * * *

UNITED STATES PATENT AND TRADEMARK OFFICE
CERTIFICATE OF CORRECTION

PATENT NO. : 9,650,324 B2  
APPLICATION NO. : 14/902698  
DATED : May 16, 2017  
INVENTOR(S) : Bellassen et al.

Page 1 of 1

It is certified that error appears in the above-identified patent and that said Letters Patent is hereby corrected as shown below:

In the Claims

At Claim 16, Column 7, Line 26, before "propanol", delete "5".

Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*